US012678120B2

(12) United States Patent
Peng et al.

(10) Patent No.: US 12,678,120 B2
(45) Date of Patent: Jul. 14, 2026

(54) METHOD AND APPARATUS FOR POSITIONING MOVABLE COMPONENT IN X-RAY IMAGING

(71) Applicant: Siemens Healthineers AG, Forchheim (DE)

(72) Inventors: Xi Shuai Peng, Shanghai (CN); Ralf Nanke, Neunkirchen am Brand (DE); Sven-Martin Sutter, Herzogenaurach (DE); Zhang Ke You, Shanghai (CN); Jing Tai Cao, Shanghai (CN)

(73) Assignee: Siemens Healthineers AG, Forchheim (DE)

( * ) Notice: Subject to any disclaimer, the term of this patent is extended or adjusted under 35 U.S.C. 154(b) by 0 days.

(21) Appl. No.: 18/833,045

(22) PCT Filed: Jan. 16, 2023

(86) PCT No.: PCT/EP2023/050810
§ 371 (c)(1),
(2) Date: Jul. 25, 2024

(87) PCT Pub. No.: WO2023/143940
PCT Pub. Date: Aug. 3, 2023

(65) Prior Publication Data
US 2025/0099064 A1      Mar. 27, 2025

(30) Foreign Application Priority Data
Jan. 28, 2022    (CN) .......................... 202210108063.3

(51) Int. Cl.
*A61B 6/00*          (2006.01)
*A61B 6/46*          (2024.01)

(52) U.S. Cl.
CPC .............. *A61B 6/547* (2013.01); *A61B 6/466* (2013.01)

(58) Field of Classification Search
CPC ................................ A61B 6/547; A61B 6/466
See application file for complete search history.

(56) References Cited

U.S. PATENT DOCUMENTS

| | | | |
|---|---|---|---|
| 4,903,204 A * | 2/1990 | Dobbins, III ......... | G06T 11/006 378/4 |
| 5,625,191 A * | 4/1997 | Nakamura ............. | A61B 6/102 250/363.04 |

(Continued)

FOREIGN PATENT DOCUMENTS

| | | |
|---|---|---|
| CN | 101889870 A | 11/2010 |
| CN | 205066775 U | 3/2016 |

(Continued)

OTHER PUBLICATIONS

Apr. 24, 2023 (PCT) International Search Report and Written Opinion—App. PCT/EP2023/050810.

*Primary Examiner* — Dixomara Vargas
(74) *Attorney, Agent, or Firm* — Banner & Witcoff, Ltd.

(57) ABSTRACT

A method and apparatus are described for positioning a movable component in X-ray imaging. The method comprises: acquiring a 3D image that is captured using a camera component and characterizes a motion process of a movable component; acquiring motion information of the movable component, detected by a motion sensor; positioning the movable component based on the 3D image and the motion information. The disclosure 3D image of the movable component may be combined with motion information of the movable component to position the movable component, so as to increase the precision of positioning of the movable component and improve image stitching quality and the precision of positioning of a detector, as well as to reduce the overlap requirements in image stitching and lower the exposure dose.

19 Claims, 5 Drawing Sheets

(56) References Cited

U.S. PATENT DOCUMENTS

| | | | | |
|---|---|---|---|---|
| 6,144,875 A * | 11/2000 | Schweikard | .......... | A61B 90/10 |
| | | | | 378/69 |
| 6,334,708 B1 * | 1/2002 | Kosugi | ................. | A61B 6/504 |
| | | | | 378/68 |
| 10,799,206 B2 | 10/2020 | Viswanathan et al. | | |
| 2003/0099328 A1 * | 5/2003 | Jensen | ................... | A61B 6/463 |
| | | | | 378/198 |
| 2009/0003528 A1 * | 1/2009 | Ramraj | ................... | A61B 6/08 |
| | | | | 378/119 |
| 2011/0054688 A1 * | 3/2011 | Ortmaier | ............... | A61B 6/102 |
| | | | | 700/255 |
| 2011/0075793 A1 * | 3/2011 | Akahori | ................ | A61B 6/469 |
| | | | | 378/4 |
| 2014/0022353 A1 * | 1/2014 | Hamersma | ............ | B25J 9/1666 |
| | | | | 348/46 |
| 2016/0196666 A1 * | 7/2016 | Venkatraghavan | ..... | G06T 7/248 |
| | | | | 382/130 |
| 2016/0278732 A1 * | 9/2016 | Amiri | ................... | A61B 6/547 |
| 2019/0217518 A1 * | 7/2019 | Mark | ................... | B29C 64/118 |
| 2020/0100758 A1 | 4/2020 | Viswanathan et al. | | |
| 2021/0145382 A1 * | 5/2021 | Schimpf | ............... | A61B 6/547 |
| 2022/0096027 A1 * | 3/2022 | Deinlein | ............. | A61B 6/4464 |
| 2022/0353409 A1 * | 11/2022 | Ma | ....................... | H04N 23/695 |
| 2023/0096023 A1 * | 3/2023 | Zucker | .................. | A61B 34/30 |
| | | | | 606/1 |
| 2023/0110248 A1 * | 4/2023 | Faraji | .................... | B25J 9/1697 |
| | | | | 700/254 |

FOREIGN PATENT DOCUMENTS

| | | | |
|---|---|---|---|
| CN | 110960234 A | 4/2020 |
| CN | 112168192 A | 1/2021 |
| DE | 202018003975 U1 | 9/2018 |
| EP | 3915481 A1 | 12/2021 |

* cited by examiner

Acquire a 3D image that is captured using a camera component and characterizes a motion process of a movable component
101

Acquire motion information of the movable component, detected by a motion sensor
102

Position the movable component based on the 3D image and the motion information
103

400

METHOD AND APPARATUS FOR POSITIONING MOVABLE COMPONENT IN X-RAY IMAGING

CROSS-REFERENCE TO RELATED APPLICATIONS

The present application is a national stage entry of PCT application no. PCT/EP2023/050810, filed Jan. 16, 2023, which claims priority to and the benefit of China patent application no. CN 202210108063.3, filed on Jan. 28, 2022, the contents of which are of which being incorporated herein by reference in their entireties.

TECHNICAL FIELD

The present disclosure relates to the technical field of medical imaging and, in particular, to a method and apparatus for positioning a movable component in X-ray imaging.

BACKGROUND

X-rays are electromagnetic radiation with a wavelength between ultraviolet rays and gamma rays. X-rays are penetrating, having different penetrating abilities for substances of different densities. In medical settings, X-rays are generally used to project organs and bones of the human body to form medical images.

An X-ray imaging system generally comprises an X-ray generating component, a Bucky Wall Stand (BWS) component, an examination table component, a cassette component comprising a plate detector, and a control master computer located remotely, etc. The X-ray generating component uses a high voltage provided by a high-voltage generator to emit X-rays, which pass through an irradiated imaging target, and forms medical image information of the imaging target on the plate detector. The plate detector sends the medical image information to the control master computer. The imaging target can stand close to the Bucky wall stand component or lie on the examination table component, so as to undergo X-ray photography of parts such as the head, chest, abdomen, and joints, respectively.

In many applications of X-ray imaging (e.g. image stitching applications or detector positioning applications, etc.), a motion sensor (e.g. a rotary encoder, inclinometer or inertial measurement unit, etc.) is generally used to measure the position of a movable component (e.g. an X-ray tube or detector, etc.). In such a method, the precision with which the movable component is positioned depends on the measurement precision of the motion sensor. However, to increase the precision with which the movable component is positioned, it is necessary to increase the precision of the motion sensor, and thus necessary to increase the hardware cost.

SUMMARY DISCLOSURE

Embodiments of the present disclosure propose a method and apparatus for positioning a movable component in X-ray imaging.

The technical solution of embodiments of the present disclosure comprises:

A method for positioning a movable component in X-ray imaging, comprising:

acquiring a 3D image that is captured using a camera component and characterizes a motion process of a movable component;

acquiring motion information of the movable component, detected by a motion sensor;

positioning the movable component based on the 3D image and the motion information.

Thus, the embodiments of the present disclosure combine the 3D image characterizing the motion process of the movable component with motion information detected by the motion sensor to position the movable component, thus increasing the positioning precision and reducing the hardware cost requirements for the motion sensor.

In one demonstrative embodiment, the movable component is an X-ray tube, and the motion sensor is arranged on the X-ray tube;

the step of positioning the movable component based on the 3D image and the motion information comprises:

updating the motion information based on the 3D image;

generating a motion path of the X-ray tube based on the updated motion information;

the method further comprises:

stitching X-ray images based on the motion path.

Thus, the 3D image and motion information may be included in a combined manner to generate a motion path of the X-ray tube, and because the precision of the motion path of the X-ray tube is increased, the precision of X-ray image stitching is also correspondingly increased, so it is possible to reduce the overlap requirements in image stitching and lower the exposure dose.

In one demonstrative embodiment, the movable component is a detector, and the motion sensor is arranged on the detector;

the step of positioning the movable component based on the 3D image and the motion information comprises:

updating the motion information based on the 3D image;

generating a motion path of the detector based on the updated motion information;

positioning the detector based on the motion path.

As can be seen, the embodiments of the present disclosure achieve precise positioning of the detector.

In one demonstrative embodiment, the movable component is a detector, and the motion sensor is arranged on the detector;

the step of positioning the movable component based on the 3D image and the motion information comprises:

generating a motion path of the detector based on the motion information;

predicting a position of the detector at a predetermined time point based on the 3D image and the motion path.

Thus, the embodiments of the present disclosure also achieve prediction of detector position, making it easier to search for the detector.

In one demonstrative embodiment, the step of predicting a position of the detector at a predetermined time point based on the 3D image and the motion path comprises:

determining an initial position of the detector based on the 3D image that is chronologically closest to the current time and includes the detector;

determining a motion trend of the detector beginning at the initial position, based on the motion path;

predicting a position of the detector at a predetermined time point based on the initial position of the detector and the motion trend of the detector.

As can be seen, by analyzing the initial position of the detector and the motion trend of the detector, it is possible to predict a position of the detector at a predetermined time point, making it easier to search for the detector quickly.

In one demonstrative embodiment, the step of positioning the movable component based on the 3D image and the motion information comprises:

determining a motion range of the movable component based on the motion information;

seeking Homonymy Points between the 3D images in a Homonymy Point query range determined on the basis of the motion range;

positioning the movable component based on the discovered Homonymy Points.

Thus, the embodiments of the present disclosure use 3D images and motion information together to position the movable component with high precision.

An apparatus for positioning a movable component in X-ray imaging, comprising:

a first acquisition module, for acquiring a 3D image that is captured using a camera component and characterizes a motion process of a movable component;

a second acquisition module, for acquiring motion information of the movable component, detected by a motion sensor;

a positioning module, for positioning the movable component based on the 3D image and the motion information.

Thus, the present disclosure combines the 3D image characterizing the motion process of the movable component with motion information detected by the motion sensor to position the movable component, thus increasing the positioning precision and reducing the hardware cost requirements for the motion sensor.

In one demonstrative embodiment, the movable component is an X-ray tube, and the motion sensor is arranged on the X-ray tube;

the positioning module is used for updating the motion information based on the 3D image;

generating a motion path of the X-ray tube based on the updated motion information; and the apparatus further comprises:

a stitching module, for stitching X-ray images based on the motion path.

Thus, the 3D image and motion information may be included in a combined manner to generate a motion path of the X-ray tube, and because the precision of the motion path of the X-ray tube is increased, the precision of X-ray image stitching is also correspondingly increased, so it is possible to reduce the overlap requirements in image stitching and lower the exposure dose.

In one demonstrative embodiment, the movable component is a detector, and the motion sensor is arranged on the detector;

the positioning module is used for updating the motion information based on the 3D image;

generating a motion path of the detector based on the updated motion information; and positioning the detector based on the motion path.

As can be seen, the embodiments of the present disclosure achieve precise positioning of the detector.

In one demonstrative embodiment, the movable component is a detector, and the motion sensor is arranged on the detector;

the positioning module is used for generating a motion path of the detector based on the motion information; and predicting a position of the detector at a predetermined time point based on the 3D image and the motion path.

Thus, the embodiments of the present disclosure also achieve prediction of detector position, making it easier to search for the detector.

In one demonstrative embodiment, the positioning module is used for determining an initial position of the detector based on the 3D image that is chronologically closest to the current time and includes the detector; determining a motion trend of the detector beginning at the initial position, based on the motion path; and predicting a position of the detector at a predetermined time point based on the initial position of the detector and the motion trend of the detector.

As can be seen, by analyzing the initial position of the detector and the motion trend of the detector, it is possible to predict a position of the detector at a predetermined time point, making it easier to search for the detector quickly.

In one demonstrative embodiment, the positioning module is used for determining a motion range of the movable component based on the motion information; seeking Homonymy Points between the 3D images in a Homonymy Point query range determined on the basis of the motion range; and positioning the movable component based on the discovered Homonymy Points.

Thus, the embodiments of the present disclosure use 3D images and motion information together to position the movable component with high precision.

An apparatus for positioning a movable component in X-ray imaging, comprising a processor and a memory;

an application program executable by the processor is stored in the memory, and used to cause the processor to perform the method for positioning a movable component in X-ray imaging as described in any one of the embodiments above.

As can be seen, the embodiments of the present disclosure propose an apparatus having a memory-processor architecture, which combines the 3D image characterizing the motion process of the movable component with motion information detected by the motion sensor to position the movable component, thus increasing the positioning precision and reducing the hardware cost requirements for the motion sensor.

A computer-readable storage medium, having computer-readable instructions stored therein, the computer-readable instructions being used to perform the method for positioning a movable component in X-ray imaging as described in any one of the embodiments above.

A computer program product, comprising a computer program which, when executed by a processor, realizes the method for positioning a movable component in X-ray imaging as described in any one of the embodiments above.

Thus, the embodiments of the present disclosure propose a computer-readable storage medium and a computer program product, which combine the 3D image characterizing the motion process of the movable component with motion information detected by the motion sensor to position the movable component, thus increasing the positioning precision and reducing the hardware cost requirements for the motion sensor.

KEY TO THE FIGURES

| Label | Meaning |
|---|---|
| 100 | method for positioning a movable component in X-ray imaging |
| 101-103 | steps |
| 21 | 3D image at time $T_0$ |
| 31 | motion information at time $T_0$ |
| 41 | updating of motion information at time $T_0$ |
| 2N | 3D image at time $T_n$ |
| 3N | motion information at time $T_n$ |
| 4N | updating of motion information at time $T_n$ |
| 51 | motion path |
| 52 | image stitching constraint condition |
| 53 | image stitching |
| 71 | 3D image at time $T_0$ |
| 81 | motion information at time $T_0$ |
| 7N | 3D image at time $T_n$ |
| 8N | motion information at time $T_n$ |
| 91 | motion state image at time $T_0$ |
| 9N | motion state image at time $T_n$ |
| 400 | apparatus for positioning a movable component in X-ray imaging |
| 401 | first acquisition module |
| 402 | second acquisition module |
| 403 | positioning module |
| 404 | stitching module |
| 500 | apparatus for positioning a movable component in X-ray imaging |
| 501 | processor |
| 502 | memory |

DETAILED DESCRIPTION

The present disclosure is explained in further detail below in conjunction with the accompanying drawings and embodiments, to clarify the technical solution and advantages thereof. It should be understood that the exemplary embodiments described here are merely intended to explain the present disclosure elaboratively, not to define the scope of protection thereof.

The solution of the present disclosure is expounded below by describing a number of representative embodiments, in order to make the description concise and intuitive. The large number of details in the embodiments are merely intended to assist with understanding of the solution of the present disclosure. However, obviously, the technical solution of the present disclosure need not be limited to these details when implemented. To avoid making the solution of the present disclosure confused unnecessarily, some embodiments are not described meticulously, but merely outlined. Hereinbelow, "comprises" means "including but not limited to", while "according to . . . " means "at least according to . . . , but not limited to only according to . . . ". In line with the linguistic customs of Chinese, in cases where the quantity of a component is not specified hereinbelow, this means that there may be one or more of the component; this may also be interpreted as meaning at least one.

In embodiments of the present disclosure, a 3D image of a movable component (e.g. a BWS, detector, patient table, X-ray tube, etc.) in an X-ray imaging system is combined with motion sensor data measured for the movable component, in order to more accurately determine the position of the movable component in the X-ray imaging system.

Figure 1:
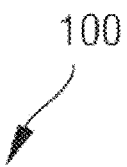
FIG. 1 illustrates a flow chart of a method for positioning a movable component in X-ray imaging according to an embodiment of the present disclosure.
Figure 1:
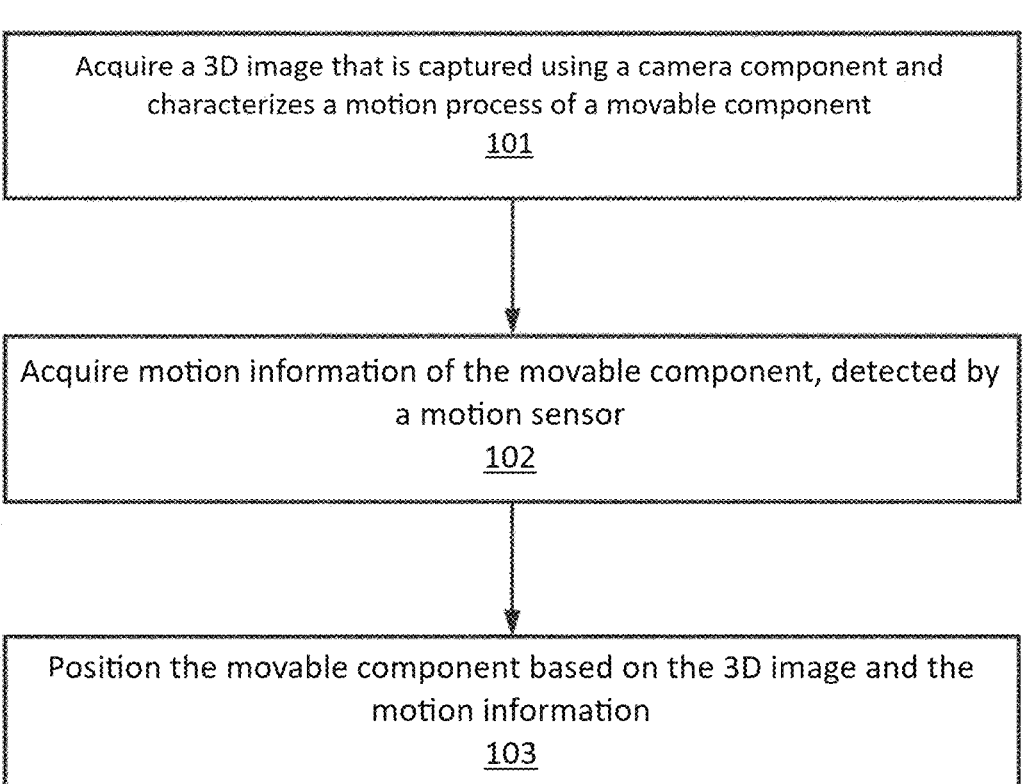

FIG. 1 illustrates a flow chart of a method for positioning a movable component in X-ray imaging according to an embodiment of the present disclosure. The method shown in FIG. 1 may be performed by a controller. The controller may be implemented as, or integrated in, a control master computer of the X-ray imaging system, or may be implemented as a control unit that is independent of the control master computer.

As shown in FIG. 1, the method 100 comprises:

Step 101: acquiring a 3D image that is captured using a camera component and characterizes a motion process of a movable component.

Here, the 3D image is generally multiple images based on a time sequence. The meaning of "characterizes a motion process of a movable component" includes at least one of the following:

(1) Content describing the motion process of the movable component is directly included in the 3D image. An example is a 3D image obtained when a camera component arranged on the X-ray tube photographs the detector. The photography target of the 3D image comprises the detector. Thus, based on the 3D image, an understanding of the motion process of the detector can be gained in a visually direct way.

(2) Content describing the motion process of the movable component is not directly included in the 3D image. Nevertheless, based on the 3D image, an understanding of the motion process of the movable component can be gained indirectly. For example, a camera component arranged on the X-ray tube photographs the scene in front of it in the direction towards the tube port to obtain a 3D image. The 3D image does not include the X-ray tube, but includes an image of the scene in front of the tube mouth. Based on the 3D image, an understanding of the motion process of the X-ray tube can be gained indirectly.

In one demonstrative embodiment, the 3D image can be acquired from a storage medium (e.g. the cloud or a local database), wherein the 3D image is captured with a camera component. Here, a light source of the camera component may or may not coincide with an X-ray source in the X-ray imaging system. When the light source of the camera component coincides with the X-ray source in the X-ray imaging system, the camera component is generally fixed to a beam limiter housing or tube cover of the X-ray generating component. For example, a recess for accommodating the camera component is arranged on the tube cover or on the housing of the beam limiter, and the camera component is fixed to the recess by bolt connection, snap-fit connection, a steel wire loop, etc. When the light source of the camera component does not coincide with the X-ray source in the X-ray imaging system, the camera component may be arranged at any position suitable for photographing the subject, in an examination room in which the subject is located, e.g. on the ceiling, on the floor, or on various components in the X-ray imaging system, etc.

In one embodiment, the camera component comprises at least one 3D camera. The 3D camera uses 3D imaging technology to capture a 3D image characterizing the motion process of the movable component. In one embodiment, the camera component comprises at least two 2D cameras, each of which is respectively arranged at a predetermined position. In practice, those skilled in the art can select a suitable position as the predetermined position to arrange the 2D camera as required. The camera component may further comprise an image processor. The image processor synthesizes a 3D image of the subject from 2D images captured by the 2D cameras, wherein a depth of field used by the image processor during synthesis may be a depth of field of any 2D image. Optionally, each 2D camera may send respectively captured 2D images to an image processor outside the camera component, for the image processor outside the camera component to synthesize a 3D image of the subject from the 2D images captured by the 2D cameras, wherein a depth of field used by the image processor outside the camera component during synthesis may likewise be a depth of field of any 2D image. Specifically, the image processor outside the camera component may be implemented as a control master computer in the X-ray imaging system, or as an independent control unit separate from the X-ray imaging system.

In one embodiment, the camera component may comprise: at least one 2D camera and at least one depth of field sensor. The at least one 2D camera and at least one depth of field sensor are installed at the same position. The camera component may further comprise an image processor. The image processor uses a depth of field provided by the depth of field sensor and a 2D photograph provided by the 2D camera together to generate a 3D image characterizing the motion process of the movable component. Optionally, the 2D camera sends a captured 2D image of the subject to an image processor outside the camera component, and the depth of field sensor sends an acquired depth of field to the image processor outside the camera component, for the image processor outside the camera component to use the depth of field and the 2D photograph together to generate a 3D image of the subject. The image processor outside the camera component may be implemented as a control master computer in the X-ray imaging system, or as an independent control unit separate from the X-ray imaging system.

After acquiring the 3D image, the camera component may send the 3D image via a wired interface or wireless interface to a controller, which performs the procedure in FIG. 1. The wired interface may comprise at least one of the following: a universal serial bus interface, controller local area network interface or serial port, etc.; the wireless interface may comprise at least one of the following: an infrared interface, near field communication interface, Bluetooth interface, Zigbee interface, wireless broadband interface, etc.

Typical examples of the camera component photographing the subject to generate a 3D image have been described demonstratively above, but those skilled in the art will realize that such descriptions are merely demonstrative and not intended to define the scope of protection of the embodiments of the present disclosure.

Step 102: acquiring motion information of the movable component, detected by a motion sensor.

The motion sensor may be used to measure various types of motion information of the movable component, e.g. triaxial attitude angle (or angular velocity), acceleration and translation amount, etc. The motion sensor may comprise: a rotary encoder, an inertial measurement unit (IMU), a gyroscope or an inclinometer, etc.

Step 103: positioning the movable component based on the 3D image and the motion information.

In one demonstrative embodiment, positioning the movable component based on the 3D image and the motion information in step 103 comprises: determining a motion range of the movable component based on the motion information; seeking Homonymy Points between 3D images in a Homonymy Point query range determined on the basis of the motion range; and positioning the movable component based on discovered Homonymy Points. Thus, the embodiments of the present disclosure use 3D images and motion information together to position the movable component with high precision.

For example, suppose that the motion information indicates that the X-ray tube has moved 10 cm downwards; then it is determined that the motion range is [0 cm, −10 cm]. Taking error into account, the Homonymy Point query range is generally greater than the motion range; for example, the Homonymy Point query range may be [5 cm, −15 cm]. Homonymy Points between 3D images are then sought in the range of [5 cm, −15 cm], and the X-ray tube is positioned based on discovered Homonymy Points; for example, it is found that the X-ray tube has moved 8 cm downwards. Positioning information determined on the basis of the 3D images is then used to determine that the X-ray tube has moved 8 cm downwards.

Thus, the embodiments of the present disclosure combine the 3D image characterizing the motion process of the movable component with motion information detected by the motion sensor to position the movable component, thus increasing the positioning precision and reducing the hardware cost requirements for the motion sensor.

In one embodiment, the movable component is an X-ray tube, and the motion sensor is arranged on the X-ray tube; positioning the movable component based on the 3D image and the motion information in step 103 comprises: updating the motion information based on the 3D image; generating a motion path of the X-ray tube based on the updated motion information; and the method 100 further comprises: stitching X-ray images based on the motion path. Thus, the 3D image and motion information may be included in a combined manner to generate a motion path of the X-ray tube, and because the precision of the motion path of the X-ray tube is increased, the precision of X-ray image stitching is also correspondingly increased, so it is possible to reduce the overlap requirements in image stitching and lower the exposure dose.

In one embodiment, the movable component is a detector, and the motion sensor is arranged on the detector; positioning the movable component based on the 3D image and the motion information in step 103 comprises: updating the motion information based on the 3D image; generating a motion path of the detector based on the updated motion information; and positioning the detector based on the motion path. As can be seen, the embodiments of the present disclosure achieve precise positioning of the detector.

In one demonstrative embodiment, the movable component is a detector, and the motion sensor is arranged on the detector; positioning the movable component based on the 3D image and the motion information in step 103 comprises: generating a motion path of the detector based on the motion information; and predicting a position of the detector at a predetermined time point based on the 3D image and the motion path. Thus, the embodiments of the present disclosure also achieve prediction of detector position, making it easier to search for the detector.

In one demonstrative embodiment, predicting a position of the detector at a predetermined time point based on the 3D image and the motion path comprises: determining an initial position of the detector based on a 3D image that is chronologically closest to the current time and includes the detector; determining a motion trend of the detector beginning at the initial position, based on the motion path; and predicting a position of the detector at a predetermined time point based on the initial position of the detector and the motion trend of the detector. As can be seen, by analysing the initial position of the detector and the motion trend of the detector, it is possible to predict a position of the detector at a predetermined time point, making it easier to search for the detector quickly.

Embodiments of the present disclosure have been described demonstratively above, taking as examples the cases where the movable component is implemented as an X-ray tube and as a detector. Those skilled in the art will realize that such a description is merely demonstrative, and not intended to limit the scope of protection of embodiments of the present disclosure.

Figure 2:
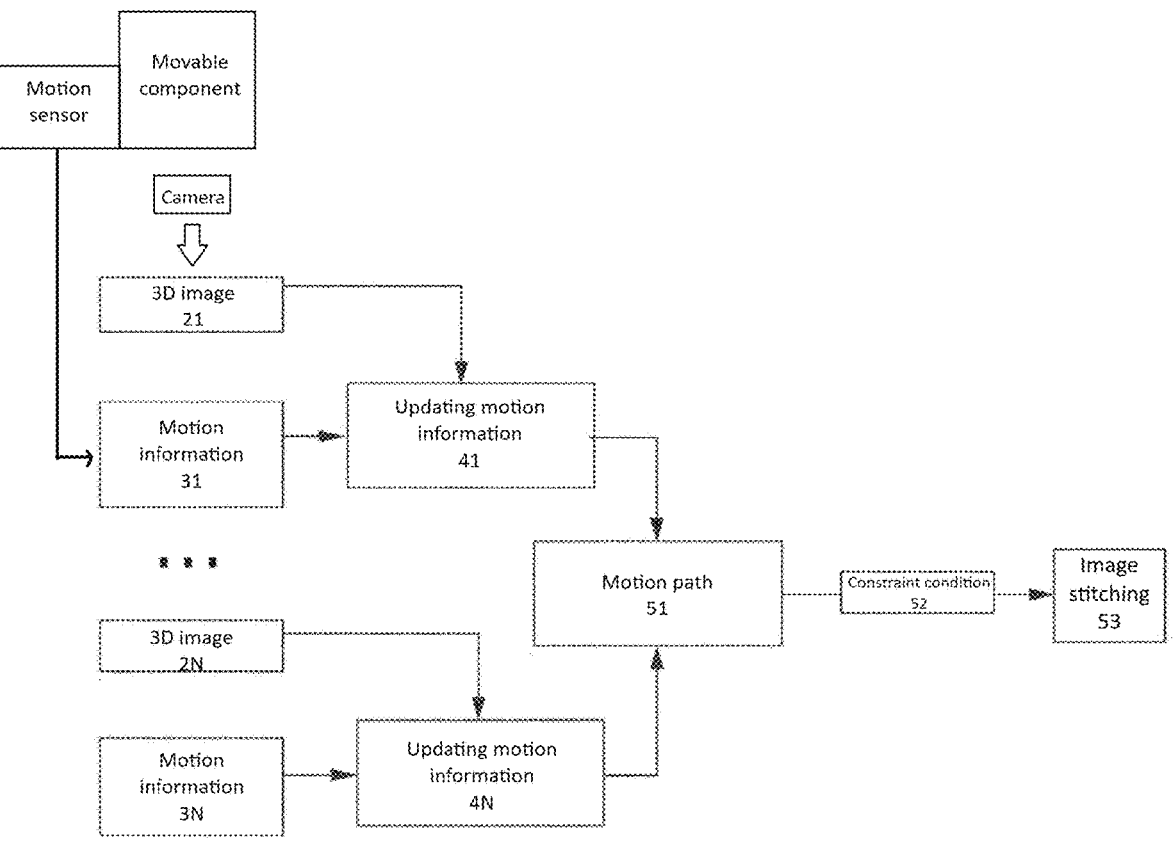
FIG. 2 illustrates a demonstrative flow chart of stitching X-ray images according to an embodiment of the present disclosure.

FIG. 2 illustrates a demonstrative flow chart of stitching X-ray images according to an embodiment of the present disclosure. In FIG. 2, within a time range formed with a time T0 as a starting point and a time Tn as an end point, a camera component continuously captures 3D images characterizing a motion process of a movable component, and a motion sensor continuously detects motion information of the movable component.

The camera component captures a 3D image 21 at time T0. The 3D image 21 characterizes a motion state of the movable component at time T0, as captured by the camera component. The motion sensor detects motion information 31 at time T0. The motion information 31 characterizes a motion state of the movable component at time T0, as detected by the motion sensor. Similarly, the camera component captures a 3D image 2N at time Tn. The 3D image 2N characterizes a motion state of the movable component at time Tn, as captured by the camera component. The motion sensor detects motion information 3N at time Tn. The motion information 3N characterizes a motion state of the movable component at time Tn, as detected by the motion sensor.

For each time in the time range, the 3D image at that time is used to update the motion information for that time. For example, in the updating of motion information 41, the 3D image 21 is used to update the motion information 31. Similarly, in the updating of motion information 4N, the 3D image 2N is used to update the motion information 3N. The updated motion information corresponding to each time is then used to generate a motion path 51 of the movable component. The motion path 51 is then added to a constraint condition 52 used to constrain image stitching 53, and image stitching 53 is performed.

Figure 3:
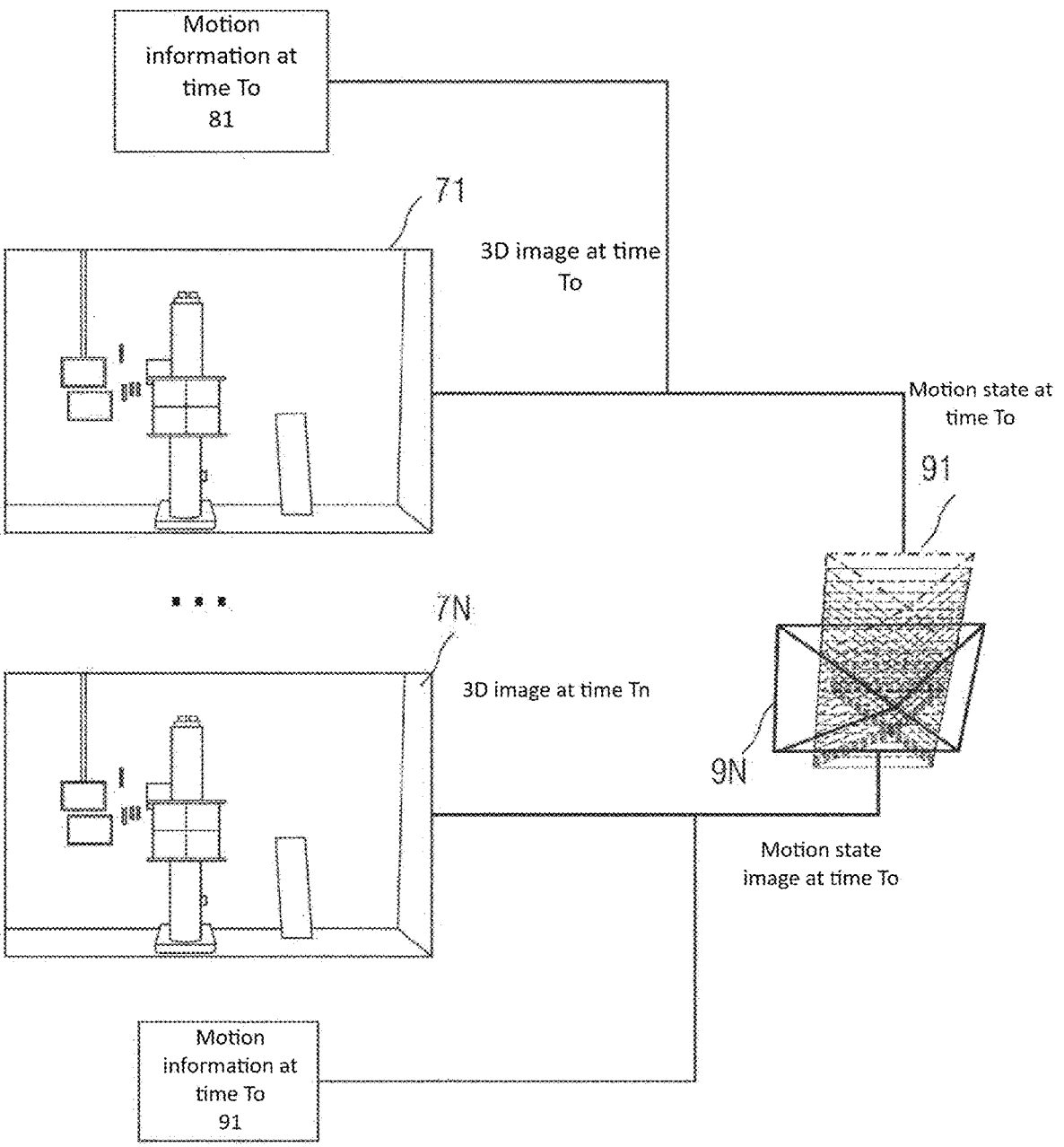
FIG. 3 illustrates a schematic diagram of determining a motion path of an X-ray tube according to an embodiment of the present disclosure.

FIG. 3 illustrates a schematic diagram of determining a motion path of an X-ray tube according to an embodiment of the present disclosure.

In FIG. 3, a path state image 91 corresponding to time T0 is generated by Simultaneous Localization and Mapping (SLAM) based on a 3D image 71 of the X-ray tube at time T0 and motion information of the X-ray tube at time T0. Similarly, for each time following time T0, a path state image corresponding to that time can be generated, until a path state image 9N corresponding to time Tn is generated based on a 3D image 7N at time Tn and motion information at time Tn. Based on analysis of the change in state in the process from the path state image 91 to the path state image 9N, a motion path of the X-ray tube can be determined.

Figure 4:
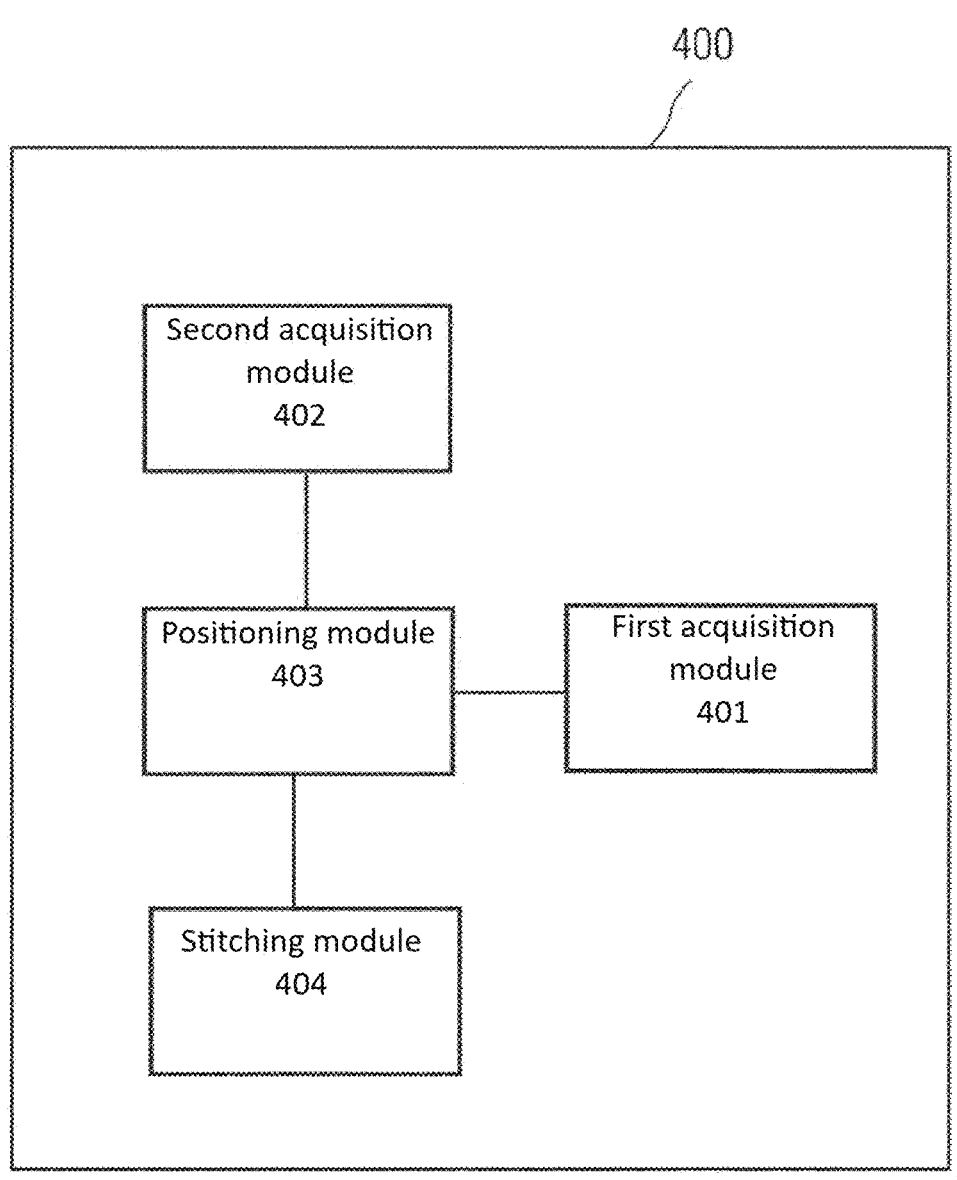
FIG. 4 illustrates a structural diagram of an apparatus for positioning a movable component in X-ray imaging according to an embodiment of the present disclosure.

FIG. 4 illustrates a structural diagram of an apparatus for positioning a movable component in X-ray imaging according to an embodiment of the present disclosure.

As shown in FIG. 4, an apparatus 40 for positioning a movable component in X-ray imaging comprises:

a first acquisition module 401, for acquiring a 3D image that is captured using a camera component and characterizes a motion process of a movable component;

a second acquisition module 402, for acquiring motion information of the movable component, detected by a motion sensor;

a positioning module 403, for positioning the movable component based on the 3D image and the motion information.

In one demonstrative embodiment, the movable component is an X-ray tube, and the motion sensor is arranged on the X-ray tube; the positioning module 403 is used for updating the motion information based on the 3D image; generating a motion path of the X-ray tube based on the updated motion information; and the apparatus 400 further comprises: a stitching module 404, for stitching X-ray images based on the motion path.

In one demonstrative embodiment, the movable component is a detector, and the motion sensor is arranged on the detector; the positioning module 403 is used for updating the motion information based on the 3D image; generating a motion path of the detector based on the updated motion information; and positioning the detector based on the motion path.

In one demonstrative embodiment, the movable component is a detector, and the motion sensor is arranged on the detector; the positioning module 403 is used for generating a motion path of the detector based on the motion information; and predicting a position of the detector at a predetermined time point based on the 3D image and the motion path.

In one demonstrative embodiment, the positioning module 403 is used for determining an initial position of the detector based on a 3D image that is chronologically closest to the current time and includes the detector; determining a motion trend of the detector beginning at the initial position, based on the motion path; predicting a position of the detector at a predetermined time point based on the initial position of the detector and the motion trend of the detector.

In one demonstrative embodiment, the positioning module 403 is used for determining a motion range of the movable component based on the motion information; seeking Homonymy Points between 3D images in a Homonymy Point query range determined on the basis of the motion range; and positioning the movable component based on discovered Homonymy Points.

Figure 5:
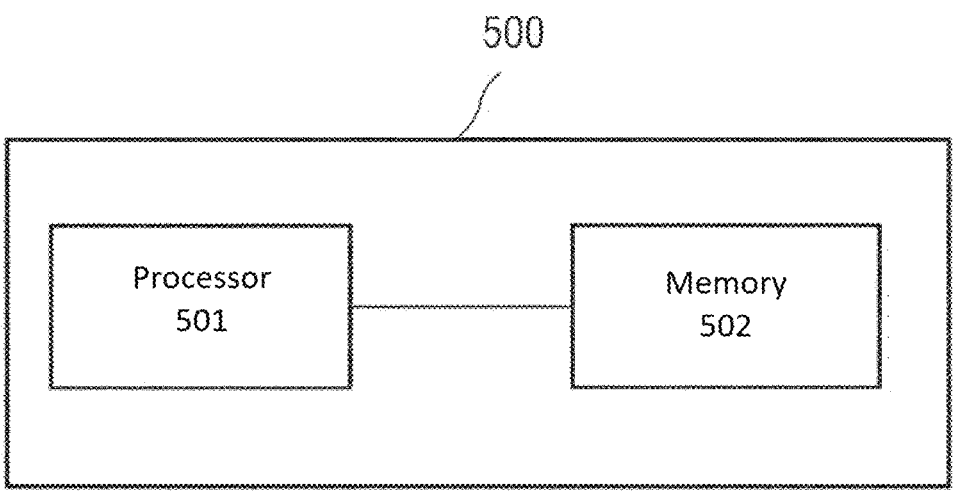
FIG. 5 illustrates a structural diagram of an apparatus for positioning a movable component in X-ray imaging, having a memory-processor architecture, according to an embodiment of the present disclosure.

FIG. 5 illustrates a structural diagram of an apparatus for positioning a movable component in X-ray imaging, having a memory-processor architecture, according to an embodiment of the present disclosure.

As shown in FIG. 5, apparatus 500 for positioning a movable component in X-ray imaging comprises a processor 501, a memory 502, and a computer program that is stored on the memory 502 and capable of being run on the processor 501; when executed by the processor 501, the computer program implements the method for positioning a movable component in X-ray imaging according to any one of the embodiments above. The memory 502 may specifically be implemented as various types of storage media, such as an electrically erasable programmable read-only memory (EEPROM), a flash memory or a programmable read-only memory (PROM). The processor 501 may be implemented as comprising one or more central processors or one or more field-programmable gate arrays, wherein the field-programmable gate array integrates one or more central processor cores. Specifically, the central processor or central processor core may be implemented as a CPU or MCU or DSP, etc.

It must be explained that not all of the steps and modules in the flows and structural diagrams above are necessary;

certain steps or modules may be omitted according to actual requirements. The order in which steps are executed is not fixed, but may be adjusted as required. The partitioning of the modules is merely functional partitioning, employed for the purpose of facilitating description; during actual implementation, one module may be realized by multiple modules, and the functions of multiple modules may be realized by the same module; these modules may be located in the same device, or in different devices.

Hardware modules in the embodiments may be realized mechanically or electronically. For example, one hardware module may comprise a specially designed permanent circuit or logic device (such as a dedicated processor, such as an FPGA or ASIC) for completing a specific operation. The hardware module may also comprise a programmable logic device or circuit that is temporarily configured by software (e.g. comprising a general processor or another programmable processor) for executing a specific operation. The choice of whether to specifically use a mechanical method, or a dedicated permanent circuit, or a temporarily configured circuit (e.g. configured by software) to realize the hardware module can be decided according to considerations of cost and time.

The present disclosure also provides a machine-readable storage medium, in which is stored an instruction for causing a machine to execute the method described herein. Specifically, a system or apparatus equipped with a storage medium may be provided; software program code realizing the function of any one of the embodiments above is stored on the storage medium, and a computer (or CPU or MPU) of the system or apparatus is caused to read and execute the program code stored in the storage medium. Furthermore, it is also possible to cause an operating system etc. operating on a computer to complete a portion of, or all, actual operations by means of an instruction based on program code. It is also possible for program code read out from the storage medium to be written into a memory installed in an expansion board inserted in the computer, or written into a memory installed in an expansion unit connected to the computer, and thereafter instructions based on the program code cause a CPU etc. installed on the expansion board or expansion unit to execute a portion of and all actual operations, so as to realize the function of any one of the embodiments above. Embodiments of storage media used for providing program code include floppy disks, hard disks, magneto-optical disks, optical disks (such as CD-ROM, CD-R, CD-RW, DVD-ROM, DVD-RAM, DVD-RW, DVD+RW), magnetic tapes, non-volatile memory cards and ROM. Optionally, program code may be downloaded from a server computer or a cloud via a communication network.

The embodiments above are example embodiments of the present disclosure, which are not intended to define the scope of protection of the present disclosure. Any amendments, equivalent substitutions or improvements etc. made within the spirit and principles of the present disclosure shall be included in the scope of protection thereof.

The various components described herein may be referred to as "units," "modules," or "components." Such components may be implemented via any suitable combination of hardware and/or software components as applicable and/or known to achieve their intended respective functionality. This may include mechanical and/or electrical components, processors, processing circuitry, or other suitable hardware components, in addition to or instead of those discussed herein. Such components may be configured to operate independently, or configured to execute instructions or computer programs that are stored on a suitable computer-readable medium. Regardless of the particular implementation, such units or subunits, as applicable and relevant, may alternatively be referred to herein as "circuitry," "controllers," "processors," or "processing circuitry," or alternatively as noted herein.

The invention claimed is:

1. A method, comprising:
   positioning a movable component associated with a component of an X-ray imaging system by:
      acquiring a three-dimensional (3D) image that is captured via a camera and characterizes a motion process of the movable component;
      acquiring motion information of the movable component that is detected by a motion sensor; and
   positioning the movable component based on the 3D image and the motion information by:
      determining a motion range of the movable component based on the motion information;
      identifying homonymy points between 3D images in a homonymy point query range that is determined on the basis of the motion range; and
      positioning the movable component based on the identified homonymy points.

2. The method as claimed in claim 1, wherein:
   the movable component comprises an X-ray tube,
   the motion sensor is arranged on the X-ray tube, and
   the positioning the movable component based on the 3D image and the motion information further comprises:
      updating the motion information based on the 3D image; and
      generating a motion path of the X-ray tube based on the updated motion information.

3. The method as claimed in claim 1, wherein:
   the movable component comprises a detector,
   the motion sensor is arranged on the detector, and
   the positioning the movable component based on the 3D image and the motion information further comprises:
      updating the motion information based on the 3D image;
      generating a motion path of the detector based on the updated motion information; and
      positioning the detector based on the motion path.

4. The method as claimed in claim 1, wherein:
   the movable component comprises a detector,
   the motion sensor is arranged on the detector, and
   the positioning the movable component based on the 3D image and the motion information further comprises:
      generating a motion path of the detector based on the motion information; and
      predicting a position of the detector at a predetermined time point based on the 3D image and the motion path.

5. The method as claimed in claim 4, wherein predicting the position of the detector at the predetermined time point comprises:
   determining an initial position of the detector based on the 3D image that is chronologically closest to a current time and includes the detector;
   determining a motion trend of the detector beginning at the initial position based on the motion path; and
   predicting a position of the detector at the predetermined time point based on the initial position of the detector and the motion trend of the detector.

6. An apparatus for positioning a movable component associated with a component of an X-ray imaging system, comprising:

first acquisition circuitry configured to acquire a three-dimensional (3D) image that is captured via a camera and characterizes a motion process of the movable component;

second acquisition circuitry configured to acquire motion information of the movable component that is detected by a motion sensor; and positioning circuitry configured to position the movable component based on the 3D image and the motion information by:

determining a motion range of the movable component based on the motion information;

identifying homonymy points between 3D images in a homonymy point query range determined on the basis of the motion range; and positioning the movable component based on the identified homonymy points.

7. The apparatus as claimed in claim 6, wherein:

the movable component comprises an X-ray tube, the motion sensor is arranged on the X-ray tube, and the positioning circuitry is further configured to update the motion information based on the 3D image and to generate a motion path of the X-ray tube based on the updated motion information.

8. The apparatus as claimed in claim 6, wherein:

the movable component comprises a detector, the motion sensor is arranged on the detector, and the positioning circuitry is further configured to update the motion information based on the 3D image, to generate a motion path of the detector based on the updated motion information, and to position the detector based on the motion path.

9. The apparatus as claimed in claim 6, wherein:

the movable component comprises a detector, the motion sensor is arranged on the detector, and the positioning circuitry is further configured to generate a motion path of the detector based on the motion information and to predict a position of the detector at a predetermined time point based on the 3D image and the motion path.

10. The apparatus as claimed in claim 9, wherein the positioning circuitry is configured to:

determine an initial position of the detector based on a 3D image that is chronologically closest to a current time and includes the detector;

determine a motion trend of the detector beginning at the initial position based on the motion path; and predict a position of the detector at a predetermined time point based on the initial position of the detector and the motion trend of the detector.

11. A non-transitory computer-readable storage medium having computer-readable instructions stored thereon that, when executed by a processor of an apparatus for positioning a movable component associated with a component of an X-ray imaging system, cause the apparatus to:

acquire a three-dimensional (3D) image that is captured via a camera and characterizes a motion process of the movable component;

acquire motion information of the movable component that is detected by a motion sensor; and position the movable component based on the 3D image and the motion information by:

determining a motion range of the movable component based on the motion information;

identifying homonymy points between 3D images in a homonymy point query range determined on the basis of the motion range; and positioning the movable component based on the identified homonymy points.

12. The method as claimed in claim 2, further comprising:

stitching X-ray images based on the motion path.

13. The apparatus as claimed in claim 7, further comprising:

stitching circuitry configured to stitch X-ray images based on the motion path.

14. The method of claim 1, wherein the-acquiring the 3D image comprises capturing, as one or more visible light images, the 3D image via the camera.

15. The method of claim 1, wherein the homonymy point query range is greater than the motion range of the movable component.

16. The method as claimed in claim 1, wherein:

the movable component comprises an X-ray tube and the motion sensor is arranged on the X-ray tube, and further comprising:

predicting a position of the X-ray tube at a predetermined time point based on the 3D image and a motion path of the X-ray tube; and positioning the X-ray tube based on the 3D image and the motion information by searching for a current position of the X-ray tube using the predicted position of the X-ray tube at the predetermined time point.

17. The method of claim 1, wherein the motion sensor comprises an inertial measurement unit (IMU).

18. The method of claim 1, wherein the homonymy point query range constrains a search space for identifying the homonymy points based on the motion range.

19. The method of claim 1, wherein positioning the movable component based on the identified homonymy points comprises determining a position of the movable component based on the identified homonymy points, and wherein the determined position differs from a position indicated by the motion information.

* * * * *